United States Patent
Hietala

(10) Patent No.: US 12,420,049 B2
(45) Date of Patent: Sep. 23, 2025

(54) AIRWAY ADAPTOR WITH LIQUID CONTAINMENT PATH

(71) Applicant: GE Precision Healthcare LLC, Wauwatosa, WI (US)

(72) Inventor: Mika Harri Juhani Hietala, Espoo (FI)

(73) Assignee: GE Precision Healthcare LLC, Wauwatosa, WI (US)

( * ) Notice: Subject to any disclaimer, the term of this patent is extended or adjusted under 35 U.S.C. 154(b) by 948 days.

(21) Appl. No.: 17/547,397

(22) Filed: Dec. 10, 2021

(65) Prior Publication Data

US 2023/0181860 A1    Jun. 15, 2023

(51) Int. Cl.
    A61M 16/08    (2006.01)
    A61B 5/08     (2006.01)
    A61B 5/097    (2006.01)

(52) U.S. Cl.
    CPC ........... *A61M 16/085* (2014.02); *A61B 5/082* (2013.01); *A61B 5/097* (2013.01); *A61M 16/0808* (2013.01); *A61M 16/0816* (2013.01); *A61B 2562/225* (2013.01); *A61M 2240/00* (2013.01)

(58) Field of Classification Search
    CPC ............ A61M 16/0808; A61M 16/085; A61M 16/0402; A61M 16/0816; A61M 2016/102; A61M 2016/103; A61M 2230/432; A61M 2205/3306; G01N 21/05; G01N 21/0303; G01N 21/3504; G01N 2001/2267; A61B 5/0873; A61B 5/097; A61B 5/082
    See application file for complete search history.

(56) References Cited

U.S. PATENT DOCUMENTS

| 5,213,109 A * | 5/1993 | Susi ................ A61B 5/097 73/23.3 |
| 6,935,338 B1 * | 8/2005 | Triunfo, Jr. ......... A61M 16/085 128/204.22 |
| 8,642,966 B2 | 2/2014 | Weckstrom et al. |

(Continued)

FOREIGN PATENT DOCUMENTS

| CN | 102781502 B * | 11/2015 | ........ A61M 16/1045 |
| CN | 210130841 U | 3/2020 | |
| WO | 2020077354 A1 | 4/2020 | |

OTHER PUBLICATIONS

CN 102781502 machine translation (Year: 2015).*

(Continued)

*Primary Examiner* — Victoria Murphy
*Assistant Examiner* — Sara K Toich
(74) *Attorney, Agent, or Firm* — Andrus Intellectual Property Law, LLP

(57) ABSTRACT

An airway adaptor providing a measurement chamber for gas measurement by a mainstream gas analyzer includes a body having a first end and a second end and configured to connect in a ventilation circuit carrying ventilation gas to and from a patient. The body forms a primary path that includes the measurement chamber and is configured to allow ventilation gas to pass between the first end and the second end and at least one secondary path separated from the primary path and located on an outer perimeter of the primary path. The at least one secondary path is configured to contain liquid away from the measurement chamber.

20 Claims, 4 Drawing Sheets

(56) References Cited

U.S. PATENT DOCUMENTS

| | | | |
|---|---|---|---|
| 2010/0154797 A1* | 6/2010 | Landis | A61M 16/0463 128/205.27 |
| 2011/0028858 A1 | 2/2011 | Dainobu | |
| 2014/0330154 A1* | 11/2014 | Haveri | A61M 16/085 |
| 2015/0238119 A1* | 8/2015 | Colman | A61B 5/097 29/428 |
| 2015/0320962 A1* | 11/2015 | Bafile | A61M 16/0057 128/204.18 |
| 2018/0242883 A1* | 8/2018 | Friberg | A61M 16/0003 |
| 2020/0116632 A1* | 4/2020 | Henderson | G01N 21/15 |
| 2021/0109084 A1 | 4/2021 | Hietala | |

OTHER PUBLICATIONS

CN210130841U—English Abstract; Espacenet search results Aug, 10, 2023; 1 page.

EP application 22210114.9 filed Nov. 29, 2022—extended Search Report issued May 11, 2023; 18 pages.

\* cited by examiner

AIRWAY ADAPTOR WITH LIQUID CONTAINMENT PATH

BACKGROUND

The present disclosure generally relates to respiratory gas sensor systems that measure one or more respiratory gas components in a breathing circuit of a patient, and more particularly to respiratory sensor systems having a gas analyzer that includes color detection systems for component identification.

In anesthesia and in intensive care, the condition of a patient is often monitored by analyzing the gas inhaled and exhaled by the patient for its content. For this reason, either a small portion of the respiratory gas is delivered to a gas analyzer or the gas analyzer is directly connected to the respiratory circuit. In a non-dispersive infrared (NDIR) gas analyzer, the measurement is based on the absorption of infrared (IR) radiation in the gas sample. A radiation source directs a beam of infrared radiation through a measuring chamber to a radiation detector whose output signal depends on the strength of the absorption of the radiation in the sample gas.

The radiation source typically comprises an electrically heated filament or surface area and radiation collecting optics and emits radiation within a spectral region. The gas sample to be analyzed is fed through the measuring chamber. The measuring chamber can be a tubular space, for example, with inlet and outlet for the sample gas and provided with windows that are transparent at the measurement IR wavelength and permit transmission of the IR wavelength through the chamber. Radiation is absorbed by the gas sample when passing through the measuring chamber, and thus the amount of the measurement IR wavelength that is transmitted through the chamber (i.e., from one window to the other) is indicative of certain gas component amount(s) in the gas sample.

The radiation detector generates an electrical signal that depends on the radiation power falling on its sensitive area. The detector type in a gas analyzer depends on its measurement wavelength. For measurement within a broad spectral range, a thermal detector is convenient because its sensitivity only depends on the efficiency of the conversion of radiation to heat. To make the detector's output signal sensitive to a certain gas component, the wavelength band of the radiation coming to the detector is selected so that the gas component absorbs radiation within it. This selection is made using an optical bandpass filter whose bandwidth may be, for example, 1%-2% of the center wavelength.

Gas analyzers can be configured to measure different gas components. The absorption of the gas sample is measured at a wavelength band selected to match the absorption spectra of the gas component(s) of interest. Measurement of more than one gas component can be accomplished by using one radiation detector and by changing the optical bandpass filters on the optical path in succession. It is also possible to use several radiation detectors, combined with corresponding bandpass filters. Different respiratory gases have widely spaced wavelength regions of absorption. Carbon dioxide and nitrous oxide can be measured between 3900 nm and 4600 nm whereas anesthetic agents absorb in the 8000 nm to 10,000 nm region.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, an airway adaptor providing a measurement chamber for gas measurement by a mainstream gas analyzer includes a body having a first end and a second end and configured to connect in a ventilation circuit carrying ventilation gas to and from a patient. The body forms a primary path that includes the measurement chamber and is configured to allow ventilation gas to pass between the first end and the second end and at least one secondary path separated from the primary path and located on an outer perimeter of the primary path. The at least one secondary path is configured to contain liquid away from the measurement chamber.

One embodiment of a neonatal airway adaptor providing a measurement chamber for gas measurement within the neonatal ventilation circuit by a mainstream gas analyzer has a body with a first end and a second end and configured to connect in the neonatal ventilation circuit carrying ventilation gas to and from a neonate patient. The body forms a primary path that includes the measurement chamber and is configured to allow the ventilation gas to pass between the first end and the second end, and at least one secondary path located on an outer perimeter of the primary path. The at least one secondary path is separated from the primary path and configured such that a flow rate through the secondary path is less than a flow rate through the primary path. For example, a volume of the secondary path may not exceed 20% of the volume of the primary path. The at least one secondary path is configured to contain liquid away from the measurement chamber.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
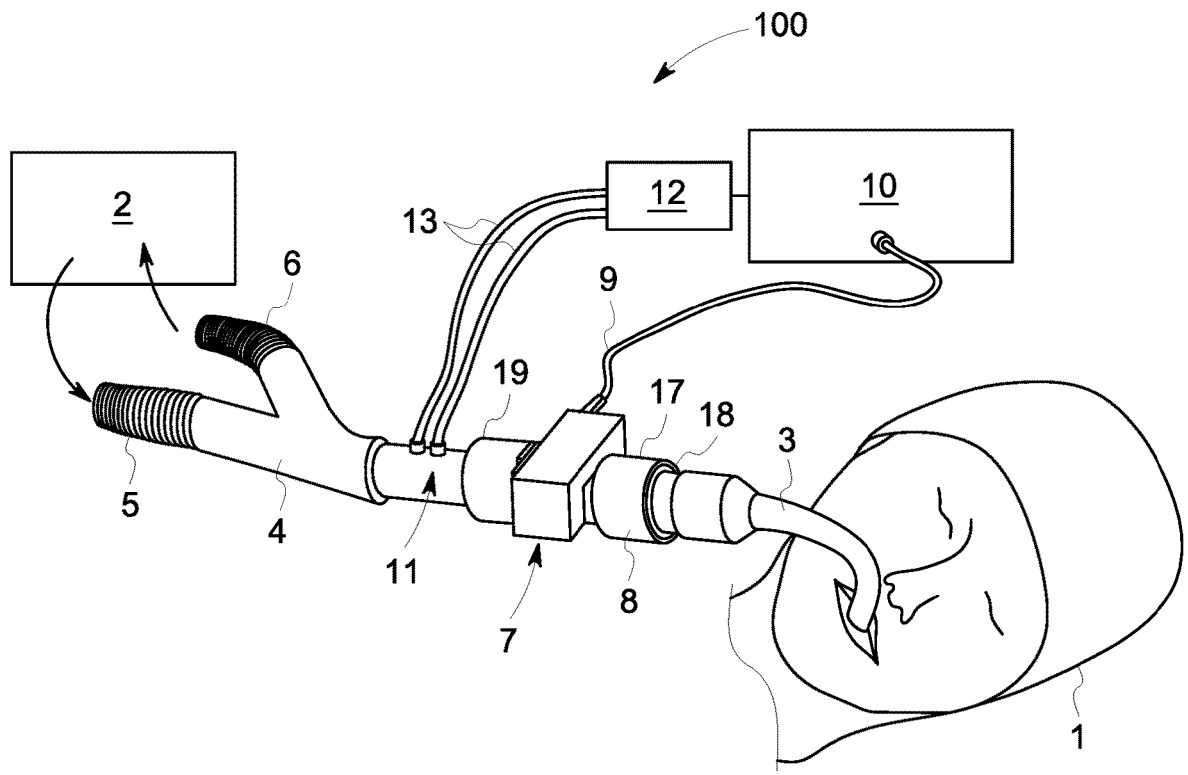
FIG. 1 illustrates a mainstream gas analyzer connected to an airway adaptor in a ventilation circuit ventilating a patient.

The present inventor has recognized that a problem with existing airway adaptors, or cuvettes, for facilitating gas measurement by a mainstream gas analyzer is that liquids and vapors collect inside the measurement chamber of the airway adaptor. The liquids accumulate on the windows of the airway adaptor through which the gas analyzer makes measurements such that accurate measurements cannot be performed by the gas analyzer. This is particularly a problem for neonatal airway adaptors where the measurement chamber and connection path through the neonatal airway adaptor has a smaller volume than for an adult airway adaptor to reduce the dead space in the neonatal ventilation circuit. In neonatal airway adaptors, the optical window size is typically the same size as used for adult cuvettes and thus the windows occupy a larger portion relative on the side of the measurement chamber and thus accumulation of liquids in the measurement chamber quickly and significantly impacts performance of gas measurements by the gas analyzer. Given the smaller volume and the proportionally larger window size, problems with liquid accumulation in neonatal gas measurement applications are particularly prevalent. A greater proportion of liquid accumulated in the neonatal ventilation circuit tends to hit the neonatal airway adaptor windows than in the adult airway adaptors and liquid in the measurement path, such as the path of the infrared transmission, attenuates the radiation and prevent accurate gas measurement.

In view of the foregoing problems and challenges in the relevant art, the inventor developed the disclosed airway adaptor having a separate path for accumulated liquid that is configured to contain accumulated liquids away from the primary path. The disclosed airway adaptor has a primary path that includes the measurement chamber and is configured to allow the ventilation gas to pass through the airway adaptor from end to end. The airway adaptor includes at least one secondary path separated from the primary path, wherein the at least one secondary path is configured to contain liquid away from the primary path to isolate as much of the accumulated liquid as possible away from the measurement chamber and particularly optical windows. Thus, the one or more secondary paths are positioned such that most, or as much as possible, of the liquid flows through the secondary path, or is otherwise contained in the secondary path away from the measurement chamber.

In various embodiments, the secondary path may extend the full length of the airway adaptor between the first end and the second end or may be configured such that the secondary path only extends a portion of the length of the airway adaptor. The at least one secondary path is located along an outer perimeter of the primary path. For example, the at least one secondary path may be on a lower half or bottom side of the body below the primary path where liquid has a greater tendency to accumulate due to gravity. In one embodiment, the secondary path may be centered below the primary path on a bottom side of the body. In another embodiment, multiple secondary paths may be distributed on a lower half of the outer perimeter of the primary path.

The system may be configured such that the airway adaptor is positioned at an angle, such as at an angle away from the patient where the end of the airway adaptor on the patient side is higher than the end of the airway adaptor on the ventilator side. In such an embodiment, system may be configured such that the liquid is channeled out of the second end, the ventilator end, of the airway adaptor away from the patient. Alternatively, in embodiments where the airway adaptor is in a horizontal position, liquid may accumulate and be maintained in the secondary path and remain there. If the liquid accumulation volume significant, it may completely fill and block the secondary path and may even accumulate above the secondary path entrance and in the primary path. However, a substantial portion of the liquids are still maintained in the secondary path away from the primary path, and particularly away from the measurement chamber.

The secondary path, or group of secondary paths, may be configured so that it does not significantly impact the dead space created by the airway adaptor. This is particularly important for neonatal applications where minimizing dead space is important given the small lung size and breath volume of the neonatal patient. Thus, the at least one secondary path may be configured such that it restricts the flow rate therethrough to minimize dead space while still enabling collection of liquid in the secondary path. The collective flow rate through the at least one secondary path may be configured such that it is 50% or less of the flow rate through the primary path. In other embodiments, the flow rate through the one or more secondary paths does not exceed 40% of the flow rate through the primary path. In still other embodiments, the total flow rate through the secondary path does not exceed 20% of the flow rate through the primary path. In still other embodiments, the total flow rate through the at least one secondary path does not exceed 10% of the flow rate through the primary path.

To reduce flow rate through of the secondary path, and thus to reduce dead space created by the secondary path, the secondary path may have a narrowed section comprising a portion of the length of the secondary path which has a smaller cross-sectional area than the cross-sectional area of other sections of the secondary path. For example, the narrowed section may be in the center portion of the body of the airway adaptor such that the narrowed section is approximately centered along the length of the secondary path. In certain examples, the narrowed section of the secondary path may be aligned with and beneath the windows. In other embodiments the narrowed section may be elsewhere along the secondary path closer to one end.

Exemplary embodiments of the disclosed airway adaptor and system comprising the disclosed airway adaptor are shown in FIGS. 1-5B and variously discussed herein. The disclosed respiratory gas sensor system 100 includes an airway adaptor 8, or cuvette, with a secondary path configured to contain liquids that have accumulated in that area of the ventilation circuit away from the primary path where the gas analyzer 7 is conducting measurements. The airway adaptor 8 has body 17 with a top side 21 and a bottom side 22. The system 100 is generally configured such that the bottom side 22 is below the top side 21 such that gravity forces liquids downward toward the bottom side 22. The body 17 has a first end 18 and a second end 19, each end configured to attach to a respective element within the ventilation circuit. In the depicted example, the first end 18 on the patient-side of the body 17 is configured to connect to an endotracheal tube 3 and the second end 19 is configured to connect to spirometry adaptor 11 and/or to a Y-piece 4 that circulates gas to and from the ventilator 2.

The gas analyzer 7 may removably connect to the airway adaptor 8, such as by clips on the airway adaptor 8 configured to create a friction connection thereto. The top side 21 may be configured to connect to the gas analyzer 7. In the depicted examples, the adaptor body 17 includes two opposing clips 24 (FIGS. 3B, 4B, and 5B) configured to removably connect to the airway adaptor, which is positioned over the top side 21 of the center portion 28 of the airway adaptor 8 and extends over the sides of the center portion 28 so as to conduct gas measurements through the windows 14.

As exemplified in FIG. 1, a ventilation circuit with a medical gas analyzer is shown. A patient 1 is connected to a ventilator 2 using an endotracheal tube 3, a Y-piece 4, an inspiratory limb 5, and an expiratory limb 6. A gas analyzer 7 is connected to an airway adaptor 8, which is connected to the intubation tube. The gas analyzer 7 is a mainstream gas analyzer measuring gases flowing between the ventilator 2 and the patient 1 without withdrawing samples of the gas to a separate gas analyzer.

The analyzer shown in FIG. 1 is electrically connected via cable 9 to the patient monitor 10. The gas component measured may be carbon dioxide ($CO_2$), nitrous oxide ($N_2O$), or any of the volatile anesthetic agents—e.g., halothane, enflurane, isoflurane, desflurane, and sevoflurane. Additionally, there may be a spirometry adaptor 11 for measuring the gas flow in the respiratory circuit. In this example, the sensor 12 is located at the distal end of two pressure relying tubes 13. The spirometry sensor may be separately connected as in FIG. 1 or it can be integrated into the mainstream gas analyzer.

Figure 2:
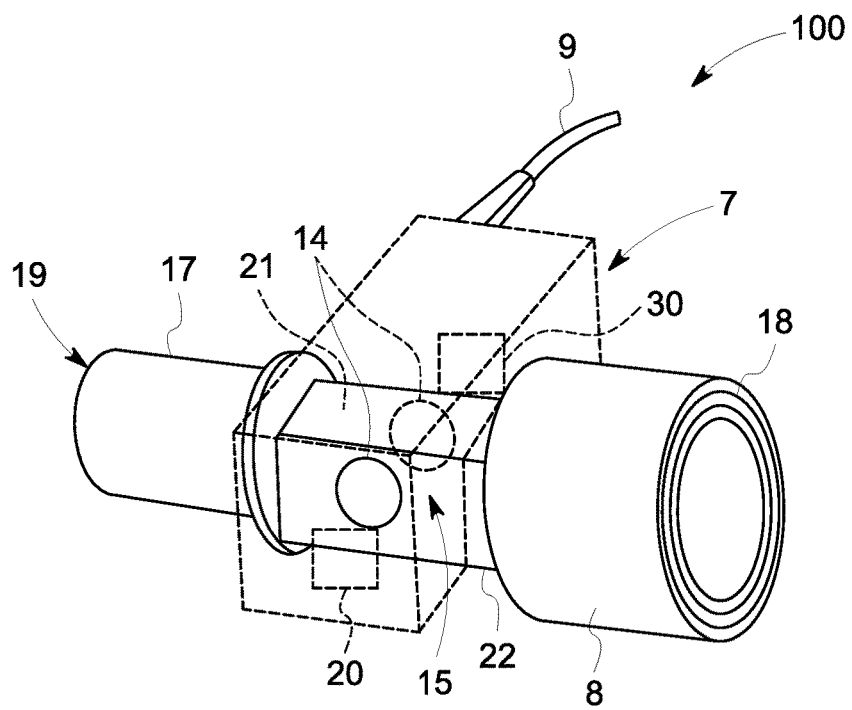
FIG. 2 shows an airway adaptor and a mainstream gas analyzer.

In FIG. 2, a different view of the gas analyzer 7 is depicted to better show the components within the gas analyzer and construction of the adaptor 8, which may be disposable or reusable. It is provided with at least one optical window 14 for allowing the IR radiation to be absorbed by the gas components in the measuring chamber between the optical windows. Typically, there are two IR-transmitting optical windows 14. IR emitter 20 is located on one side of the adaptor and one or more detector(s) 30 on the opposite side in such a way that the IR radiation is directed from the emitter 20, through the windows 14 and to the detector(s) 30.

The signals, or radiation measurement data, from each detector 30 gets amplified and modified to determine the concentration of the respiratory gas component to be measured. As mentioned above, the measured respiratory gas components can be any IR-absorbing component, such as carbon dioxide, nitrous oxide, or different volatile anesthetic agents. All these gases absorb IR radiation within some specific wavelength region and this region is selected (i.e., the measurement wavelength), such as using a narrowband filter, and the provided to the detector 30.

Figure 3A:
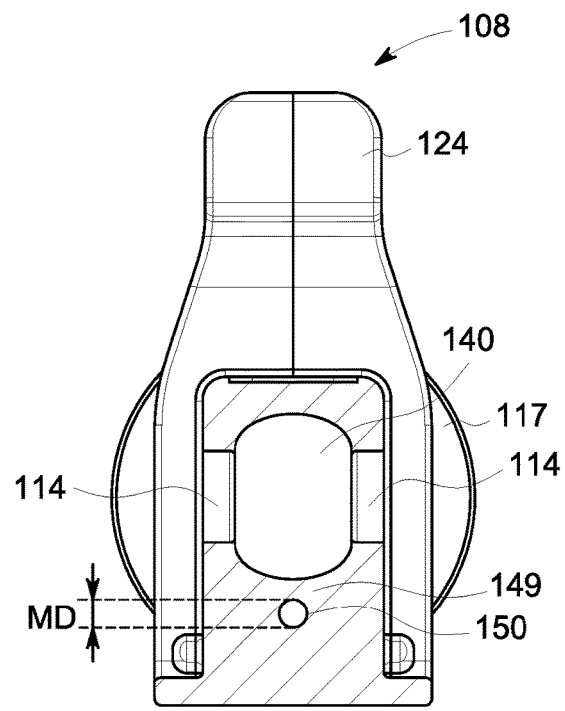
FIGS. 3A and 3B depict an exemplary neonatal airway adaptor in accordance with an embodiment of the present disclosure.
Figure 3B:
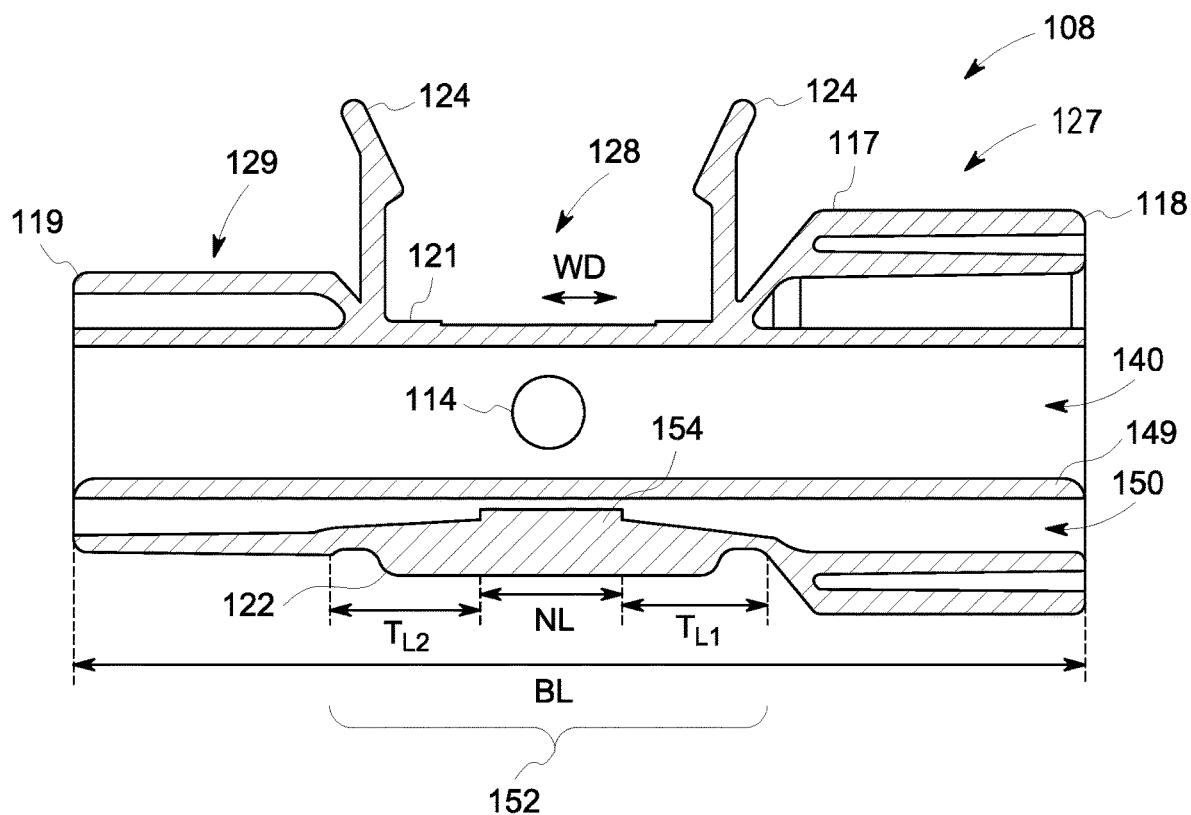
Figure 4A:
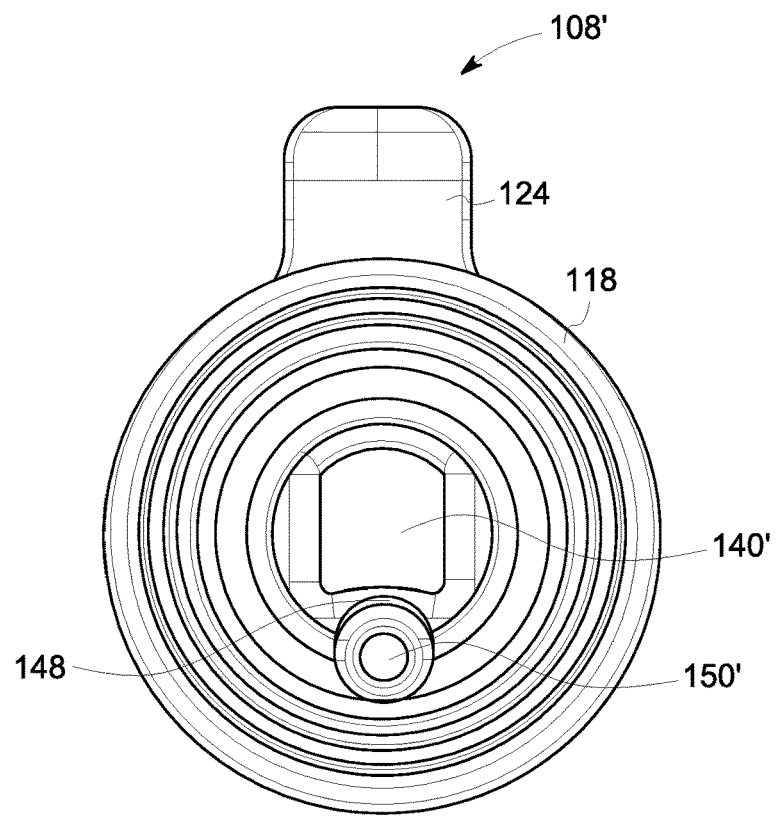
FIGS. 4A and 4B depict another embodiment of an airway adaptor in accordance with the present disclosure.
Figure 4B:
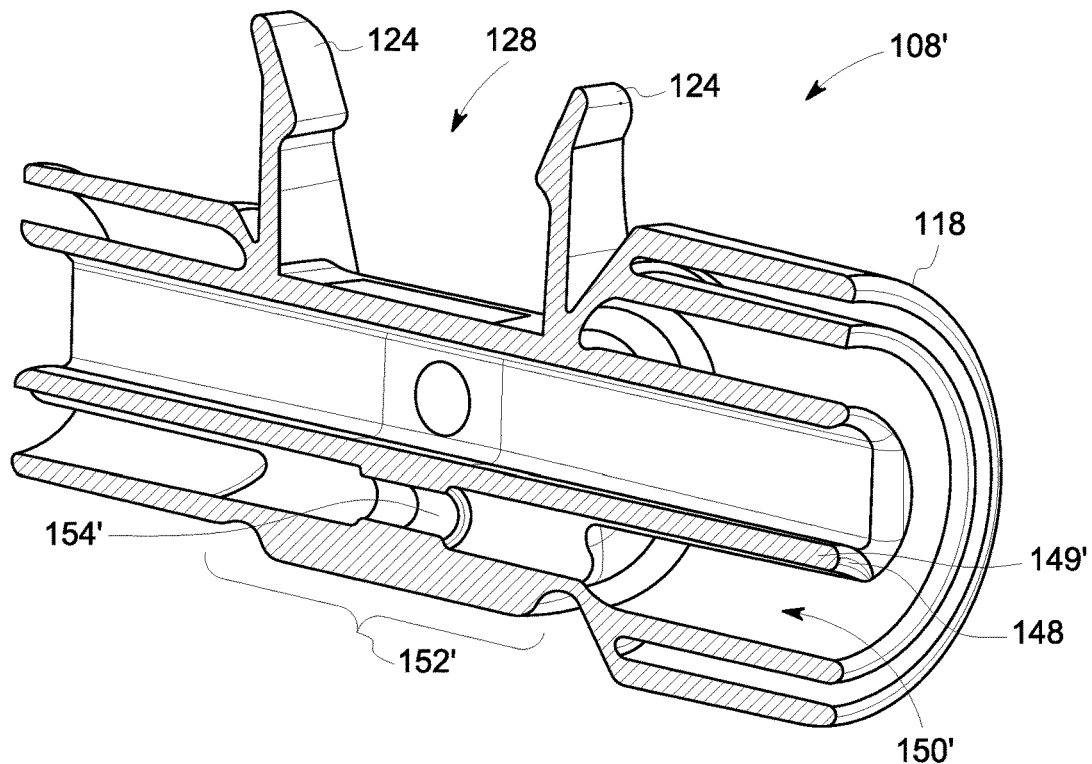
Figure 5A:
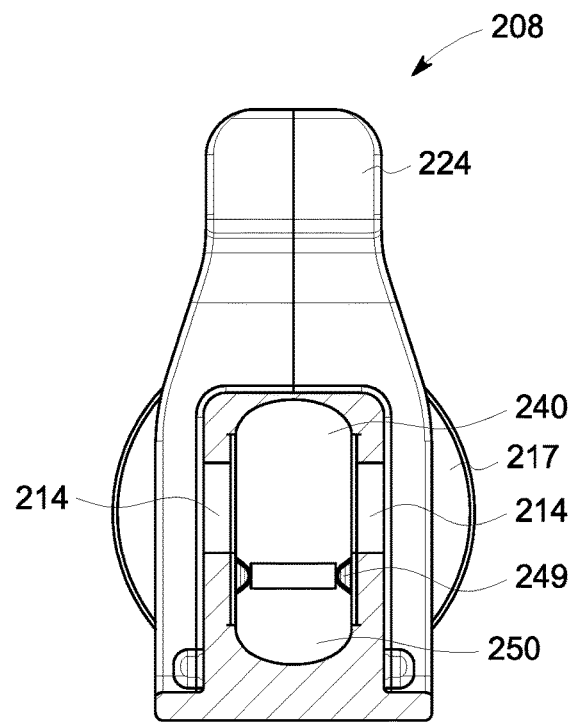
FIGS. 5A and 5B depict another embodiment of an airway adaptor in accordance with the present disclosure.
Figure 5B:
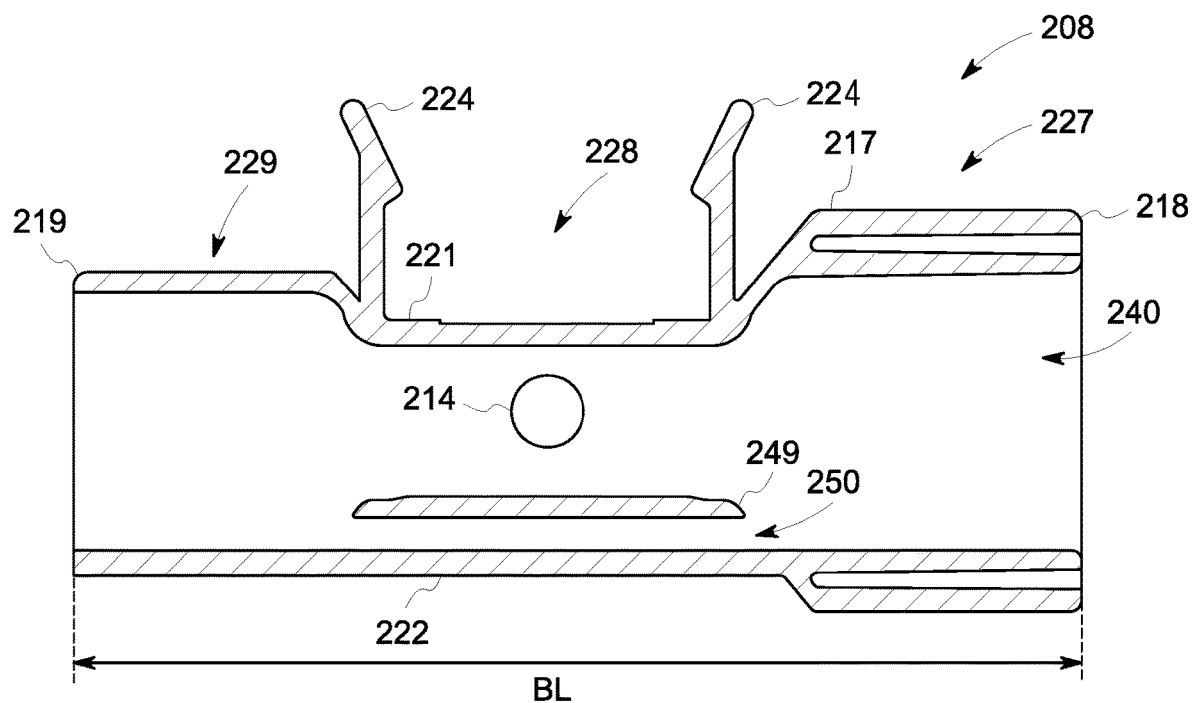

FIGS. 3A-5B depict exemplary airway adaptors 108, 108', and 208 exemplifying embodiments and features of the disclosed airway adaptor with a secondary path. FIGS. 3A and 3B depict a first exemplary neonatal adaptor 108, and FIGS. 4A and 4B depict a second exemplary neonatal adaptor 108'. FIGS. 5A-5B depict an exemplary airway adaptor 208 configured for an adult application.

FIG. 3A depicts a perpendicular cross-sectional view through a center portion of the airway adaptor and FIG. 3B depicts a cross-sectional view along the length of the neonatal airway adaptor 108. The neonatal airway adaptor 108 comprises a body 117, such as formed of a molded plastic. The body 117 has a first end 118, such as configured to connect to an endotracheal tube 3 or some other patient interface, and a second end 119, such as configured to connect to a Y-piece 4, and additional measurement section or some other element forming the neonatal ventilation circuit. The body 117 forms a patient end portion 127 from the first end 118 to a center portion 128, and a ventilator end portion 129 between the center portion and second end 119. The measurement chamber is in the center portion 128, which has two windows 114 positioned on opposing sides of the measurement chamber and configured to allow gas measurement by the mainstream gas analyzer 7. Gas analyzer 7 fits over the top side 121 of the center portion 128 and conducts gas measurements through windows 114. The airway adaptor 108 is configured to receive and connect to the gas analyzer 7 on the topside 121 via clips 124, like the arrangement shown in FIGS. 1 and 2.

The neonatal airway adaptor 108 provides a primary path 140 that includes a measurement chamber in the center section 128 configured to allow ventilation gas to pass through the measurement chamber between the first end 118 and the second end 119 of the airway adaptor body 108. The primary path 140 of the neonatal adaptor 108 has a smaller volume than a primary path for an adult airway adaptor and is configured to restrict flow through the secondary path so as to reduce the added dead space in the neonatal ventilation circuit. For example, the primary path 140 in the neonatal embodiment may be narrower than that of the adult embodiment such that it has a lesser volume and flow rate in the primary path of the neonatal airway adaptor given the smaller lung capacity of the neonate compared to an adult.

The secondary path 150 is positioned below the primary path 140 toward the bottom side 122 of the body 117. In the depicted example, one secondary path is provided. In other embodiments, two or more secondary paths may be included, such as arranged on an outer perimeter of the primary path 140. For example, two or more secondary paths may be arranged around the primary path 140, such as arranged around a lower half of the perimeter of the primary path 140 and below the windows 114.

The secondary path 150 is configured to restrict flow rate compared to that of the primary path 140. For example, the peak flow rate through the primary path 140 in the neonatal adaptor 108 may be tens of milliliter per second (mL/s), which is a common flow rate for neonatal airway adaptors. In such an example, the total flow rate through the secondary path 150 is less than 50% of the primary path flow rate. In certain examples, the flow rate through the secondary path 150 may not exceed 40%. In still further examples, the secondary path flow rate may be even more restricted, such as not exceeding 30%, 20%, or even 10% of the primary path flow rate. As described above, reducing the flow rate through the secondary path 150 is necessary to reduce the dead space created by the neonatal airway adaptor 108, and thus narrowing the secondary path significantly, may be necessary depending on the neonatal application, such as the size and development stage of the neonate. Only that part of the volume of the secondary path through which gas is traveling is calculated to be dead space volume. The volume of the portion of the secondary path that is not ventilated, i.e., has no flow pathway through the adaptor 108, is not considered to be a part of the dead space. Thus, when flow rate through the secondary path is small due to a restriction in the secondary pathway, the amount of added dead space is also small.

Where two or more secondary paths are included, the neonatal airway adaptor 108 may be configured so that the total flow rate through the secondary paths does not exceed the threshold relative flow rate through the primary path, which may be any of the forgoing examples as appropriate for the particular neonatal application and the constraints on the dead space.

Further, the one or more secondary paths 150 may be configured such that liquids accumulate and thereby reduce the available dead space. Namely, liquids accumulated in the secondary pathway 150 reduce the volume occupied by gasses, including the patient's exhalation gases, and thus the dead space is reduced over the period of use.

The depicted secondary path 150 includes a narrowed section 152. The narrowed section 152 extends for at least a portion of the length of the secondary path 150 and is configured to restrict flow rate therethrough. In the depicted example, the narrowed section 152 is positioned in the center portion 128 and is centered along the secondary path 150 below the windows 114. The narrowed section 152 has a smaller cross-sectional area than portions of the secondary path 150 that are not in the narrowed section. The narrowed section may have a consistent cross-sectional area or may have a tapered form where the cross-sectional area progressively changes—e.g., diameter MD of the secondary path 150 progressively decreases and/or increases along the length BL.

In the example at FIG. 3B, the narrowed section 152 includes three subsections, including two tapered subsections. The narrowed section 152 has a first tapered subsection having length TL1 and a second tapered subsection having length TL2 on either side of a narrowed middle subsection having length NL. The narrowed section NL is formed by a ledge 154 extending upward from the bottom wall or side of the secondary path 150 and provides a consistent, further narrowed cross-sectional area in the center of the length of the secondary path 150, which is below the windows 114.

In various embodiments, the ledge 154 may have a length NL forming the narrowed middle subsection that is at least as long as the diameter WD of the windows 114. In certain embodiments, the length NL may be 1.5 times the window diameter WD. For example, where the window diameter WD is 4 mm, the length NL may be 6 mm. In such an embodiment, the diameter MD of the narrowed middle subsection NL may be 2 mm. The restriction may be set based on the desired flow relationship between primary and secondary path.

The ledge 154 forming the narrowed middle subsection NL may extend from the bottom side of the secondary path, the top side of the secondary path, or from the surrounding perimeter such as the cross-sectional area of the narrowed middle subsection NL is circular as shown in FIG. 3A.

The cross-sectional areas of each tapered section TL1 and TL2 progressively decrease toward the center up to the ledge 154. In the depicted example, the ledge 154 and the tapered edges in the tapered section TL1 and TL2 extend from the bottom side of the secondary path 150. However, in other embodiments the ledge and tapered edges extend downward from a top side of the secondary path 150, such as from the bottom of the divider 149. In still other examples, the narrowed section may be created by protrusions from both the top and bottom sides, and/or around the entire perimeter of the secondary path 150. For example, the narrowed section 152 may have a circular cross-section across its length.

In one embodiment, the cross-sectional area may consistently decrease such that there is no ledge 154 and instead the tapered sections TL1 and TL2 extend all the way to the center. For example, the smallest cross-sectional area may be beneath the windows 114 at the approximate center of the length BL of the neonatal airway adaptor 108.

In still other embodiments, the tapering may be eliminated and the ledge 154 may extend the full length of the narrowed section 152, which may be longer or shorter than the center section 128.

In the depicted example, the narrowed section 152 extends substantially the length of the center portion 128 of the airway adaptor 108. The narrowed section 152 is centered under the windows 114. In other embodiments, the narrowed section 152 may extend for only a portion of the center portion 128, such as a portion centered under the windows 114. For example, the narrowed section 152 may be at least as long as the window diameters WD, and in some embodiments may be at least 1.5 times the window diameter WD.

In other embodiments, the narrowed section 152 may be longer than the center portion 128, such as extending into one or both of the patient end portion 27 and the ventilator end portion 129. For example, the tapered sections TL1 and TL2 may extend further outward towards the ends 118 and 119. In certain embodiments, the tapered sections TL1 and TL2 may extend all the way to the ends 118 and 119. In such an embodiment, the secondary path 150 may have a circular cross-section across its length, and the cross-section of the circle may progressively decrease toward the center between the ends 118, 119.

In the neonatal airway adaptor 108 depicted in FIGS. 3A and 3B, the secondary path 150 extends along the entire length BL of the airway adaptor 108 between the first end 118 and the second end 119. The secondary path 150 is divided and separated from the primary path 140 by divider 149. In the depicted example, the divider 149 extends the length BL between the first end 118 and the second end 119. However, in other embodiments, the divider 149 may extend only a portion of the length BL. For certain applications, and particularly for neonatal applications, it is desirable for the divider 149 to extend at least the length of the center portion 128, and in some applications extend beyond the center portion 128 and into each of the patient end portion 127 and the ventilator end portion 129. For example, the divider 149, which separates the secondary path 150 form the primary path 140, may be at least 75% of the length BL of the airway adaptor 108. In other embodiments, the divider 149 may be at least 90% of the length BL of the airway adaptor 108.

FIGS. 4A and 4B depict another exemplary neonatal airway adaptor 108'. FIG. 4A is an end view of the adaptor 108' showing the first end 148 configured to connect to the patient interface, such as the endotracheal tube 3. FIG. 4B is a perspective of a lengthwise cross-sectional view of the adaptor 108'. In the depicted embodiment, the secondary path has a cylindrical narrowed section 152' extending the length of the center portion 128. The narrowed section 152' has a consistent cross-sectional area except for a further narrowed subsection created by the ledge 154'. The divider 149' separating the primary path 150' from the secondary path 149' has a curved notch 148 at the first end which is configured to guide liquids exiting the patient airway into the secondary path 150' and away from the primary path 149'.

FIGS. 5A and 5B depict an exemplary airway adaptor 208 such as may be appropriate for ventilation measurement in an adult patient. FIG. 5A depicts a perpendicular cross-sectional view of the airway adaptor 208 and FIG. 5B depicts a longitudinal cross-sectional view of the airway adaptor 208. In this example, the divider 249 extends only a portion of the length BL' of the airway adaptor 208. Thus, the secondary path 250 extends only a portion of the length BL' of the airway adaptor 208. In the depicted example, the divider 249 extends approximately the length of the center portion 228 and does not substantially extend into the patient end portion 227 or the ventilator end portion 229.

The adult airway adaptor 208 has a larger volume primary path 240 compared to the neonatal airway adaptor 108. The primary path 240 is defined by the body 217 and extends between the first end 218 and the second end 219 of the airway adaptor 208. The airway adaptor 208 comprises a center portion 228 providing the measurement chamber and configured to receive the gas analyzer 7 and incudes clips 224 on the top side 221 of the body 217. The gas analyzer 7 fits over the top side 221 of the center portion 228 and conducts measurements through windows 214, as described above. The secondary path 250 is situated toward the bottom side 222 of the airway adaptor 208 below the primary path 240.

The secondary path 250 comprises only a portion of the length BL' of the airway adaptor 208, which in the example extends across the center portion 228 housing the measurement chamber. The divider 249 likewise extends only a portion of the length BL' and through the center portion 228. Thereby, the divider 249 creates the secondary path 250 to contain liquids away from the measurement chamber in the center portion 228, and particularly away from the windows 228. In other embodiments, the divider 249 may extend further along the length BL', such as extending the secondary path 250 partially or totally across the lengths of each of the patient end portion 27 and the ventilator end portion 29.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. An airway adaptor providing a measurement chamber for gas measurement by a mainstream gas analyzer, the airway adaptor comprising:
   a body having a first end and a second end and configured to connect in a ventilation circuit carrying ventilation gas to and from a patient;
   a primary path that includes the measurement chamber and is configured to allow the ventilation gas to pass between the first end to the second end;
   at least one secondary path separated from the primary path by a divider and located on an outer perimeter of the primary path, wherein the secondary path has an inlet and an outlet and is configured such that a flow rate of the ventilation gas through the secondary path is less than a flow rate of the ventilation gas through the primary path; and
   wherein the at least one secondary path is configured to contain liquid away from the measurement chamber.

2. The airway adaptor of claim 1, wherein the at least one secondary path is on a bottom side of the body below the primary path.

3. The airway adaptor of claim 1, wherein the at least one secondary path is separated from the primary path along at least a length of a center portion of the body.

4. The airway adaptor of claim 1, wherein the at least one secondary path runs parallel to the primary path.

5. The airway adaptor of claim 1, wherein the at least one secondary path has a narrowed section comprising a portion of a length of the secondary path.

6. The airway adaptor of claim 5, wherein the narrowed section is in a center portion of the body.

7. The airway adaptor of claim 6, wherein the narrowed section is configured to restrict a flow rate of the ventilation gas through the at least one secondary path such that it does not exceed 50% of a flow rate of the ventilation gas through the primary path.

8. The airway adaptor of claim 7, wherein the flow rate of the ventilation gas through the at least one secondary path does not exceed 40% of the flow rate of the ventilation gas through the primary path.

9. The airway adaptor of claim 8, wherein the flow rate of the ventilation gas through the at least one secondary path does not exceed 20% of the flow rate of the ventilation gas through of the primary path.

10. The airway adaptor of claim 1, further comprising at least two secondary paths, where a total flow rate of the ventilation gas through the at least two secondary paths does not exceed 20% of the flow rate of the ventilation gas through the primary path.

11. The airway adaptor of claim 1 being a neonatal adaptor and wherein the primary path has a volume that does not exceed 2.5 mL.

12. The airway adaptor of claim 11, wherein the at least one secondary path has a narrowed section comprising a portion of a length of the secondary path configured to restrict the flow rate through the at least one secondary path, such that the flow rate of the ventilation gas through the at least one secondary path does not exceed 40% of the flow rate of the ventilation gas through the primary path.

13. A neonatal airway adaptor providing a measurement chamber for gas measurement within a neonatal ventilation circuit by a mainstream gas analyzer, the airway adaptor comprising:
    a body having a first end and a second end and configured to connect in the neonatal ventilation circuit carrying ventilation gas to and from a neonate patient;
    a primary path that includes the measurement chamber and is configured to allow the ventilation gas to pass between the first end to the second end;
    at least one secondary path separated from the primary path by a divider and located on an outer perimeter of the primary path, wherein the secondary path has an inlet and an outlet and is configured such that a flow rate of the ventilation gas through the secondary path is less than a flow rate of the ventilation gas through the primary path; and
    wherein the at least one secondary path is configured to contain liquid away from the measurement chamber.

14. The neonatal airway adaptor of claim 13, wherein the at least one secondary path connects between the first end and the second end and is separated along at least a length of a center portion of the body.

15. The neonatal airway adaptor of claim 13, wherein the at least one secondary path runs parallel to the primary path between the first end and the second end.

16. The neonatal airway adaptor of claim 13, wherein the at least one secondary path is on a bottom side of the body below the primary path.

17. The neonatal airway adaptor of claim 13, wherein the at least one secondary path has a narrowed section comprising a portion of a length of the secondary path.

18. The neonatal airway adaptor of claim 17, wherein the narrowed section is in a center portion of the body.

19. The neonatal airway adaptor of claim 13, further comprising at least two secondary paths.

20. The neonatal airway adaptor of claim 19, wherein a total flow rate of the ventilation gas through the at least two secondary paths does not exceed 40% of a flow rate of the ventilation gas through the primary path.

* * * * *